(12) United States Patent
Danner et al.

(10) Patent No.: US 7,452,470 B2
(45) Date of Patent: Nov. 18, 2008

(54) METHOD OF PREPARING A FINELY DIVIDED EMULSION FROM A CRUDE EMULSION

(75) Inventors: Thomas Danner, Erpolzheim (DE);
Hartwig Voβ, Frankenthal (DE);
Andreas Bauder, Mannheim (DE);
Sonja Viereck, Mannheim (DE)

(73) Assignee: BASF SE, Ludwigshafen (DE)

( * ) Notice: Subject to any disclaimer, the term of this patent is extended or adjusted under 35 U.S.C. 154(b) by 314 days.

(21) Appl. No.: 11/280,465

(22) Filed: Nov. 17, 2005

(65) Prior Publication Data

US 2006/0102553 A1    May 18, 2006

(30) Foreign Application Priority Data

Nov. 17, 2004    (DE) ........................ 10 2004 055 542

(51) Int. Cl.
*B01D 61/00*    (2006.01)
*A23D 7/00*    (2006.01)

(52) U.S. Cl. ........................ 210/651; 210/650; 426/601; 426/602

(58) Field of Classification Search ................ 210/650, 210/651, 490, 500.25, 500.26, 321.78, 500.23; 426/601, 602, 650, 611, 612, 630, 36; 424/450; 264/4.3

See application file for complete search history.

(56) References Cited

U.S. PATENT DOCUMENTS

| | | | | |
|---|---|---|---|---|
| 4,111,812 A * | 9/1978 | Baddour | ................... | 210/257.2 |
| 4,426,293 A * | 1/1984 | Mason et al. | ................ | 210/636 |
| 4,655,927 A * | 4/1987 | Ford | ............................ | 210/639 |
| 4,737,323 A * | 4/1988 | Martin et al. | ................. | 264/4.3 |
| 4,748,288 A * | 5/1988 | Bitter et al. | .................. | 585/818 |
| 4,804,538 A * | 2/1989 | Chen | ............................ | 424/401 |
| 4,846,742 A * | 7/1989 | Bertram et al. | ............ | 440/61 R |
| 4,886,603 A * | 12/1989 | Taylor | ......................... | 210/641 |
| 4,971,696 A * | 11/1990 | Abe et al. | .............. | 210/500.25 |
| 5,352,363 A * | 10/1994 | Shibano | ...................... | 210/651 |
| 5,366,631 A * | 11/1994 | Adiletta | ....................... | 210/651 |
| 5,439,592 A * | 8/1995 | Bellos et al. | ................. | 210/651 |
| 5,501,741 A * | 3/1996 | McMahon | ..................... | 134/13 |
| 5,707,673 A * | 1/1998 | Prevost et al. | ................ | 426/417 |
| 5,773,103 A * | 6/1998 | Ciora et al. | .................. | 428/34.6 |
| 5,932,091 A * | 8/1999 | Tompkins et al. | .............. | 210/97 |
| 6,248,809 B1 * | 6/2001 | Buckley et al. | .............. | 523/310 |
| 6,471,869 B1 * | 10/2002 | Yanou et al. | ................. | 210/651 |
| 6,752,925 B2 * | 6/2004 | Bolduan | ...................... | 210/243 |
| 7,018,539 B2 * | 3/2006 | Mairal et al. | ................. | 210/651 |

FOREIGN PATENT DOCUMENTS

WO    WO97/31708    *    4/1997

OTHER PUBLICATIONS

"Preparation of Corn Oil/Water and Water/Corn Oil Emulsions Using PTFE Membranes" Suzuki et al., *Food Science Technol., Int.*, Tokyo, vol. 4(2), pp. 164-167, 1998.

"Characteristics of the Membrane Emulsification Method Combined with Preliminary Emulsification for Preparing Corn Oil-in-Water Emulsions" Suzuki et al., *Food Science Technol., Int.*, 2(1), pp. 43-47, 1996.

* cited by examiner

*Primary Examiner*—Ana M Fortuna
(74) *Attorney, Agent, or Firm*—Connolly Bove Lodge & Hutz LLP

(57) ABSTRACT

A method of preparing a finely divided emulsion from a crude emulsion is proposed where the crude emulsion is forced through a porous membrane, wherein the porous membrane is constructed from two or more superimposed layers which differ in pore diameter.

9 Claims, 1 Drawing Sheet

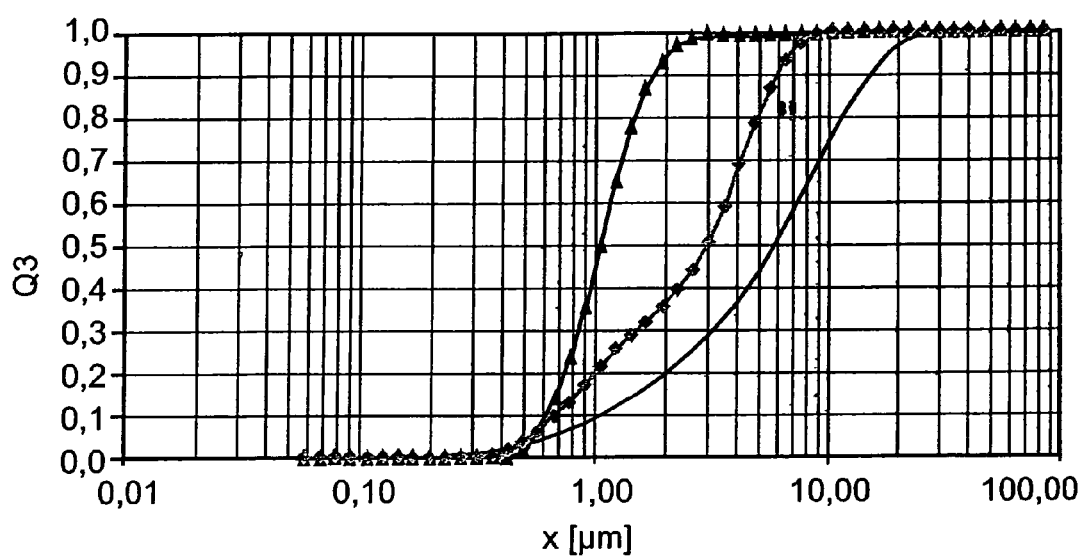

METHOD OF PREPARING A FINELY DIVIDED EMULSION FROM A CRUDE EMULSION

The present invention relates to a method of preparing a finely divided emulsion from a crude emulsion, where the crude emulsion is forced through a porous membrane.

Emulsions are used widely in the pharmaceutical, food and cosmetics industry. The properties of emulsions, such as stability and rheological behavior, are influenced to a particular extent by the droplet size distribution in the emulsion. Thus, the stability of oil-in-water or of water-in-oil emulsions increases as the droplet size distribution becomes narrower. A particular emphasis when generating emulsions is accordingly on the droplet size distribution and the average droplet size diameter.

Conventional emulsifying methods are based on a droplet size reduction for the production of oil-in-water emulsions or water-in-oil emulsions. Rotor-stator systems and high-pressure homogenization are known. Both are characterized by a high input of mechanical energy, which is problematical particularly for sensitive materials.

In contrast to this, during membrane emulsification, droplets are generated directly in which a disperse phase is forced through the pores of a porous membrane into a continuous phase. The type of membrane and its pore size distribution influences the emulsion produced and its characterizing parameters. The membranes used have been developed largely for separation tasks (membrane filtration) and are only of limited suitability for the relatively new membrane emulsification. The use of hydrophilic and hydrophobic polytetrafluoroethylene filters, microporous glass and porous ceramic (home page of the Friedrich-Schiller University of Jena, Faculty of Food Technology) is known.

The fraction of disperse phase in an emulsion cannot be increased arbitrarily with known membrane emulsification since it is no longer possible to produce an emulsion or a stable emulsion. In the case of an increased disperse phase fraction, the use of emulsifiers, additives or narrow process conditions also does not lead to the desired emulsion properties.

Food Sci. Technol., Int., 2 (1), 43-47, 1996 discloses a so called premix membrane emulsifying method which uses a crude emulsion as disperse phase. As a result, an improvement in the membrane emulsification is achieved since the fraction of disperse phase can be varied within a wider range. The input of additional energy into the continuous phase for influencing the droplet formation on the membrane is also not required.

Food Sci. Technol. Int. Tokyo, 4 (2), 164-167, 1998 discloses the use of polytetrafluoroethylene membranes which are available both with hydrophilic and also hydrophobic character. The pore size distribution of these polytetrafluoroethylene membranes is broader than for porous glass membranes. The membranes known therefrom, however, are not suitable for universal use on an industrial scale since for this the requirements for stability and throughput are higher.

In contrast, it is an object of the invention to provide a method for the premix membrane emulsification which produces, from a crude emulsion, a finely divided emulsion using porous membranes which permit industrial and universal use.

This object is achieved by a method of producing a finely divided emulsion from a crude emulsion, where the crude emulsion is forced through a porous membrane, wherein the porous membrane is constructed from two or more superimposed layers which differ in their pore diameter.

In the method according to the invention, a porous membrane is thus used which has an asymmetrical two- or more-layered construction. These may be conventional ultrafiltration and microfiltration membranes.

The mechanical stability of the membrane is based on a coarsely pored first layer (lower structure). It is self-supporting and pressure-stable without the need for a supporting device. Moreover, it serves as a carrier for one or more further layers. The coarsely pored first layer faces a finely pored second layer which is thinner than the first layer and which can be referred to as the dispersing layer. Between the two layers, further layers can be arranged whose pore diameters are preferably between that of the lower structure and that of the dispersing layer. The porous membrane is thus preferably formed from a first coarsely pored layer and one or more superimposed layers which are thinner than the first layer and have a pore diameter which is smaller than that of the first layer.

Preferably, two or more layers are applied to the first coarsely pored layer; their pore diameter decreases with increasing distance from the first layer.

Blockage of the membrane is largely prevented by such an asymmetric structure.

It is possible to produce the membrane according to the invention with an asymmetric structure starting from a symmetrical membrane by slurrying suspensions onto the symmetrical membrane. This method permits the buildup of layers of defined pore size and distribution and adjustable layer height.

The pore diameter of the coarsely pored first layer of the membrane is advantageously in the range between 1 and 20 µm and its thickness is in the range from 0.1 to 10 mm.

The pore diameter of the dispersing layer of the membrane, which is directly related to the achieved droplet diameter of the disperse phase in the fine emulsion and of the droplet size distribution is preferably in a range from 0.01 to 5 µm. The thickness of the dispersing layer is advantageously in the range between 1 and 200 µm.

A particularly suitable pore diameter of the lower structure is in the same order of magnitude as the droplet diameter of the disperse phase of the crude emulsion.

The method involves the provision of a crude emulsion, which is preferably produced in a stirred tank reactor or a mixing line. Crude emulsion is the term used for an emulsion in which the constituents of the emulsion, i.e. of the dispersion of two immiscible liquid phases, have undergone a coarse first mixing.

In contrast, fine emulsion is understood in the present case as meaning an emulsion whose average droplet diameter is in the range from 50 nm to 100 µm, preferably in the range from 100 nm to 50 µm. The droplets can be measured by means of laser light diffraction (for example using a Malvern Mastersizer 2000 or Beckmann-Coulter LS 13320) and/or by means of dynamic light scattering, for example photon correlation spectroscopy.

The process temperatures during the method according to the invention are not limited in principle. They are preferably between 0° C. and 500° C.

The pressure to be applied in order to force the crude emulsion through the porous membrane is generated in particular by means of a pump, gas pressure or by hydrostatic height. The transmembrane pressure difference between feed side and product side, which influences the droplet diameter and the droplet size distribution, is between 0.1 bar and 1000 bar, preferably between 0.5 bar and 100 bar, particularly preferably between 1 and 50 bar.

The porous membrane can be used in very diverse geometries. For example, plane geometries, tubular geometries with an internally or externally applied finely pored dispersing layer and multi-channel geometries with two or more tubular geometries integrated into a unit, and capillary or coiled geometries are possible. The porous membrane particularly preferably has a tubular geometry with internal or external coarsely pored first layer or a plane geometry. Preference is given here to pressure-stable self-supporting membrane structures which ensure adequate pressure stability without additional supporting elements even at high transmembrane pressure differences and throughputs on an industrial scale. Supporting devices made of porous materials could lead to the coalescence and thus to an impairment of the fine dispersing.

The porous membrane is arranged in suitable pressure housing with separation of feed side and product side.

The two or more layers of the porous membrane can be formed from different materials or from the same materials.

The two or more layers can be formed from different materials or from the same materials.

Different materials can be used depending on the substance-specific requirements of the emulsifying problem to be solved. Preference is given to inorganic materials, the inorganic material being, in particular, a ceramic material chosen from the group aluminum oxide, titanium dioxide, zirconium dioxide, zirconium nitride or mixtures thereof, carbon, glass, a metal or a metal alloy.

The surface-active properties of the asymmetric membrane used can also advantageously be adapted to the substance-specific requirements of the emulsifying problem to be solved in each case: thus, for producing oil-in-water emulsions, preference is given to using hydrophilic or hydrophilicized membranes, for producing water-in-oil emulsions more likely hydrophobic membranes.

An unexpected and advantageous effect on the throughput which can be achieved, on the droplet size achieved and its distribution arises as a result of a suitable through-flow direction and suitable choice of the pore diameter in the first coarsely pored layer (lower structure) and any subsequent intermediate layers. If the feed side is on the side of the lower structure, i.e. if the crude emulsion flows firstly through the lower structure and then the finely pored dispersing layer, i.e. if the crude emulsion is forced through the porous membrane from the side of the first coarsely pored layer, a much higher throughput coupled with narrower droplet size distribution is achieved than is possible in the reverse direction, i.e. from fine to coarse.

The present method is suitable for a broad diversity of industrially relevant emulsions and microemulsions, in particular for shear-sensitive and temperature-sensitive constituents. Typically for oil-in-water emulsions in which oils, organic and inorganic melts are dispersed in aqueous solution. Water-in-oil emulsions can consist of aqueous solutions, acids, alkalis, dispersions, solvents, monomers. The field of use is very diverse, for example in the pharmaceutical industry for active ingredients, in ointments and in the food industry, in which case retention of the bioactivity of the ingredients is at the fore.

Cleaning of the porous emulsifier unit takes place without large expenditure since the membranes can be cleaned with organic or inorganic solvents and/or chemically, for example using acids, bases, oxidizing agents or reducing agents, in the incorporated state.

It has thus been found that in the premix membrane emulsification the membrane is of particular importance since on the one hand it influences the process parameters and on the other hand defines the parameters achieved in the fine emulsion. It has been found that an increase in the flow of the crude emulsion through the membrane brings with it a reduction in the average droplet size and in the droplet size distribution. The universal character of the membranes according to the invention, i.e. their variant-rich structures, chemical properties and surface properties permit a use also on an industrial scale for very diverse emulsifying tasks.

The use of an asymmetrically constructed membrane with two or more layers permits large membrane areas and high pressure differences during premix membrane emulsification when used on an industrial scale. It is thus possible to realize large membrane areas and high throughflow rates. The service lives increase.

The invention is illustrated below by reference to a drawing and a working example.

In the drawing,

FIG. 1 shows the graphical representation of the droplet size distribution of a fine emulsion for different throughflow direction through a porous membrane with two layers of different porosity.

EXAMPLE

The influence of the inflow direction of a porous membrane on the throughput and the particle size distribution achieved was investigated.

For this, a disc-shaped flat UF membrane from Inocerminc GmbH comprising α-aluminum oxide with the following construction was used:

A first coarsely pored layer (lower structure) with a thickness of about 1 mm and an average pore diameter of 3 µm, a facing finely pored layer (dispersing layer) with a thickness of about 20 µm and an average pore diameter of 60 nm and two intermediate layers with a thickness of about in each case 20 µm and increasing pore diameter.

A dispersed crude emulsion of soya oil, Lutensol® TO 10 (2% by weight) and water (dispersed phase fraction 10% by weight) was forced through this porous membrane at 30° C. and a differential pressure of 1 to 5 bar.

The crude emulsion was firstly forced through the porous membrane from the side of the coarsely pored layer, in which case a throughput of 186 kg/m$^2$/h/bar was achieved, and secondly from the side of the fine dispersing layer, with a throughput virtually 100 times lower, of only 2.1 kg/m$^2$/h/bar being measured.

The experiment thus shows that for a throughflow direction from coarse to fine a virtually 100-times higher throughput was achieved compared with the reverse throughflow direction.

Moreover, for both throughflow directions, the particle size distribution was in each case measured by laser diffraction using a Malvern Mastersizer S instrument. The experiment results are shown in FIG. 1 in a semilogarithmic diagram, the droplet diameter x in micrometers being shown on the abscissa, and the dimensionless mass sum distribution Q3 being shown on the ordinate. Curve I shows the particle size distribution for the throughflow direction from coarse to fine and curve II the significantly broader particle size distribution for the throughflow direction from fine to coarse.

We claim:

1. A method of preparing a finely divided emulsion from a crude emulsion, where the crude emulsion is prepared from two immiscible liquid phases and is forced through a porous membrane, wherein the porous membrane is constructed from two or more superimposed layers which differ in their pore diameter, one of the superimposed layers is a first coarsely pored layer, and the crude emulsion is forced through the porous membrane from the side of the first coarsely pored layer, wherein the finely divided emulsion is prepared from the crude emulsion during the forcing through the porous membrane.

2. The method as claimed in claim 1, wherein the two or more layers of the porous membrane are constructed from different materials.

3. The method as claimed in claim 1, wherein the porous membrane is formed from a first coarsely pored layer and one or more superimposed layers which are thinner than the first layer and have a smaller pore diameter than the first layer.

4. The method as claimed in claim 3, wherein two or more layers whose pore diameter decreases with increasing distance from the first layer are applied to the first coarsely pored layer.

5. The method as claimed in claim 1, wherein the disperse phase of the crude emulsion has a droplet diameter in the order of magnitude of the pore diameter of the first coarsely pored layer of the porous membrane.

6. The method as claimed in claim 1, wherein the porous membrane has a tubular geometry with internal or external coarsely pored first layer or a plane geometry.

7. A method as claimed in claim 1, wherein the porous membrane is formed from inorganic material or from two or more different inorganic materials.

8. The method as claimed in claim 7, wherein the inorganic material is a ceramic material chosen from the group aluminum oxide, titanium dioxide, zirconium dioxide, zirconium nitride or mixtures thereof, carbon, glass, a metal or a metal alloy.

9. The method as claimed in claim 1, wherein the buildup of pressure which is required to force the crude emulsion through the porous membrane is generated by means of a pump, through gas pressure or hydrostatic height.

* * * * *